(12) United States Patent
Hirosawa et al.

(10) Patent No.: US 8,435,460 B2
(45) Date of Patent: May 7, 2013

(54) STERILIZED CONNECTION APPARATUS

(75) Inventors: Yusuke Hirosawa, Kanazawa (JP); Soma Watanabe, Kanazawa (JP)

(73) Assignee: Shibuya Kogyo Co., Ltd., Kanazawa-shi, Ishikawa (JP)

( * ) Notice: Subject to any disclaimer, the term of this patent is extended or adjusted under 35 U.S.C. 154(b) by 0 days.

(21) Appl. No.: 13/334,326

(22) Filed: Dec. 22, 2011

(65) Prior Publication Data
US 2012/0183456 A1    Jul. 19, 2012

(30) Foreign Application Priority Data
Jan. 19, 2011    (JP) .................................. 2011-008756

(51) Int. Cl.
*A61L 2/00*    (2006.01)
*A61L 9/00*    (2006.01)

(52) U.S. Cl.
USPC .............................. 422/292; 422/300; 422/302

(58) Field of Classification Search .................. 422/292, 422/300, 302; 137/89, 101, 625.28; 426/476
See application file for complete search history.

(56) References Cited

U.S. PATENT DOCUMENTS
6,706,302 B1 *    3/2004    Zimmer ........................ 426/476

FOREIGN PATENT DOCUMENTS
JP    2010-195432    9/2010

* cited by examiner

*Primary Examiner* — Sean E Conley
*Assistant Examiner* — Ross Dworet
(74) *Attorney, Agent, or Firm* — Flynn, Thiel, Boutell & Tanis, P.C.

(57) ABSTRACT

A sterilized connection apparatus 4 includes a sealing unit 9 which forms a decontamination space S1 between an isolator 2 provided with a first cover body 11 and an incubator 3 provided with a second cover body 21, a decontamination medium supplying unit 10 which supplies a decontamination medium to the decontamination space S1 via a supply pipe line 41, and a discharge pipe line 43 which discharges the decontamination medium of the decontamination space S1. Since the decontamination space is formed as a circular decontamination space of a small capacity surrounding the cover bodies, decontamination can be efficiently performed.

2 Claims, 5 Drawing Sheets

STERILIZED CONNECTION APPARATUS

BACKGROUND OF THE INVENTION

1. Field of the Invention

The present invention relates to a sterilized connection apparatus, and more particularly to a sterilized connection apparatus including: sealing means for forming between a first sealed box and a second sealed box, a decontamination space used to isolate a first cover body and a second cover body from an external atmosphere; decontamination medium supplying means for supplying through a supply pipe line, a vaporized decontamination medium to the decontamination space; and a discharge pipe line used to discharge the decontamination medium of the decontamination space.

2. Description of the Prior Art

According to prior art, when a culture material is transferred,
a method is used in which an incubator is connected to an isolator and the isolator is made to communicate with a carry case while a sterilized state is maintained.

Here, when the isolator is made to communicate with the carry case, their cover bodies are decontaminated which have been exposed to an external atmosphere. For this purpose, a sterilized connection apparatus is known which includes decontamination medium supplying means for forming between the isolator and the carry case, a decontamination space of a relatively small capacity used to perform isolation from the external atmosphere, and for supplying through a gas sending pipe line, a vaporized decontamination medium to the decontamination space (Patent Document 1: Japanese Patent Laid-Open No. 2010-195432).

However, in the structure described in Patent Document 1, the decontamination space is formed while the isolator and the carry case are separated from each other. Thus, in that state, the decontamination medium is supplied to the decontamination space to perform decontamination and thereafter, the isolator and the carry case are connected.

The decontamination space formed between the isolator and the carry case separated from each other has a small capacity, but there is a need to decontaminate the decontamination space. Accordingly, it takes time to satisfactorily circulate the vaporized decontamination medium and further remove decontamination components by use of aeration.

Also, after performing decontamination of the decontamination space, a procedure is needed for coupling the cover bodies of the isolator and the carry case and then opening the cover bodies in an integrated manner, thus posing a problem that the operating procedure is complex.

SUMMARY OF THE INVENTION

To address the above problem, the present invention provides a sterilized connection apparatus in which a decontamination space is formed as a space of a small capacity surrounding cover bodies and further the decontamination space having a circular shape can be efficiently decontaminated.

That is, a sterilized connection apparatus is provided which includes: sealing means for forming between a first sealed box having an opening sealed by a first cover body and a second sealed box having an opening sealed by a second cover body, a decontamination space used to isolate the first cover body and the second cover body from an external atmosphere; decontamination medium supplying means for supplying through a supply pipe line, a vaporized decontamination medium to the decontamination space; and a discharge pipe line used to discharge the decontamination medium of the decontamination space.

The sterilized connection apparatus is characterized in that: cover body connecting means is provided which couples the first cover body and the second cover body and forms the decontamination space as a circular decontamination space surrounding the periphery of the cover bodies; a shielding member used to block circulation of the decontamination medium is provided on the inside of the circular decontamination space so that the circular decontamination space is divided to form a long and thin pipe line-shaped decontamination space having an end section constituted of the shielding member; and supply pipe lines are connected, respectively, to both end sections of the long and thin decontamination space and further, the discharge pipe line is connected between connecting positions of the supply pipe lines.

According to the above described invention, the decontamination space is formed as a circular space surrounding the periphery of the cover bodies by the cover body connecting means. Accordingly, a small space can be formed compared to the structure described in Patent Document 1. Further, immediately after completion of decontamination, the first and second cover bodies can be opened. Accordingly, a decontaminating operation can be efficiently performed.

Furthermore, the shielding member is provided on the inside of the circular decontamination space to form a long and thin pipe line-shaped decontamination space, and supply pipe lines are connected, respectively, to both end sections of the long and thin decontamination space and further, the discharge pipe line is connected between these supply pipe lines. As a result, a decontamination medium can be quickly and uniformly circulated through the whole pipe line-shaped decontamination space. Thus, decontamination can be efficiently performed.

DETAILED DESCRIPTION OF THE EMBODIMENTS

Figure 1:
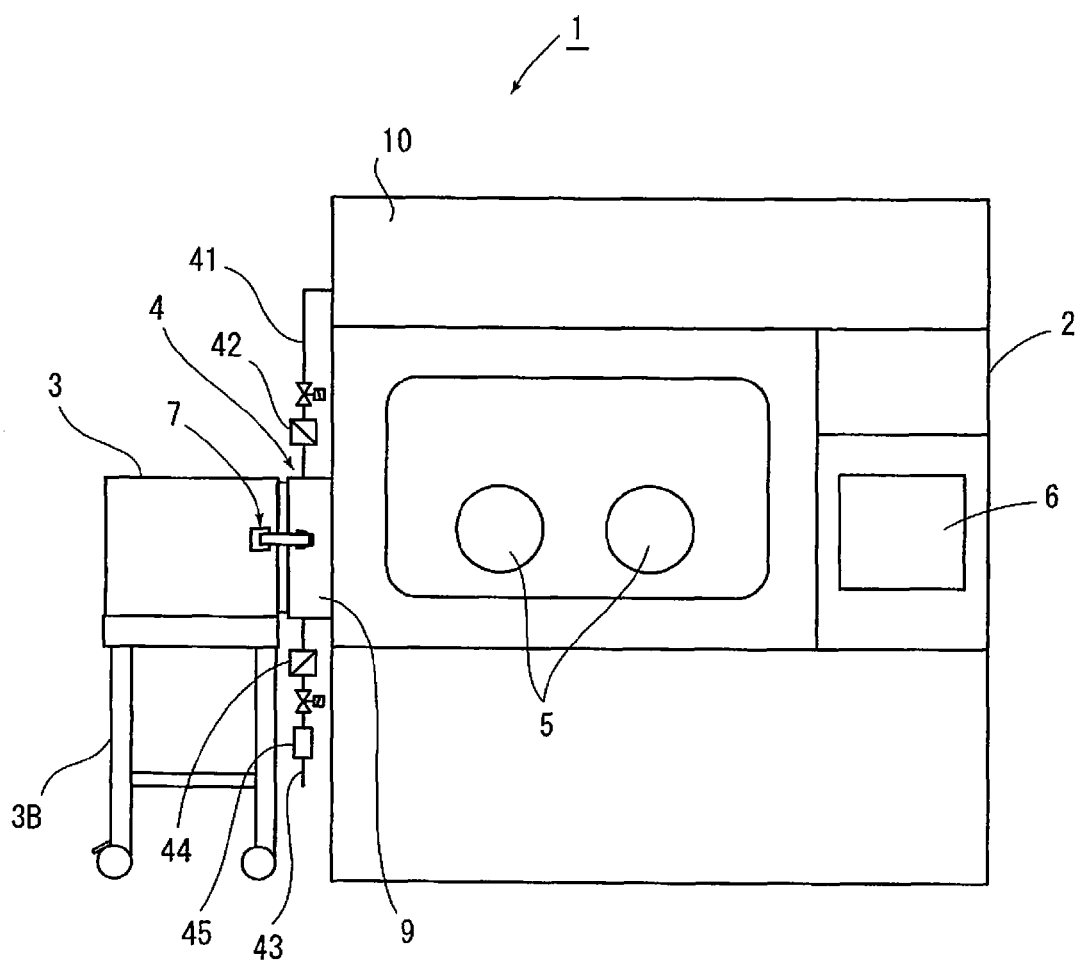
FIG. 1 is a configuration diagram of a sterilized culture system according to the present embodiment.

The present invention will be described below with reference to the drawings showing preferred embodiments thereof. FIG. 1 illustrates a sterilized culture system 1 for incubating cells or tissues. The sterilized culture system 1 includes an isolator 2 acting as a first sealed box, an incubator 3 acting as a second sealed box, and a sterilized connection apparatus 4 which connects the isolator 2 and the incubator 3 and causes the internal spaces of the isolator 2 and the incubator 3 to communicate with each other while maintaining a sterilized state.

The isolator 2 is provided with a sterilized air supplying unit (not illustrated) which supplies sterilized air, and with a decontamination unit (not illustrated) which supplies a vaporized decontamination medium such as hydrogen peroxide vapor. Before and after use of the isolator 2, the internal space of the isolator 2 is decontaminated by a decontamination medium supplied by the decontamination unit. When the isolator 2 is used, its internal space is pressurized by the sterilized air so that the sterilized state of the internal space is maintained.

The isolator 2 is also provided with a glove 5 which is worn by an operator to perform a sterilizing operation, and with a pass box 6 used for decontaminating and receiving instruments, samples and the like used in the internal space of the isolator 2.

The internal space 3A of the incubator 3 contains a culture case. Further, the incubator 3 can move while being mounted on a wagon 3B.

Gas, such as carbon dioxide, suitable for incubation is supplied from the outside to the incubator 3. The gas is blown out into the internal space 3A by a fan (not illustrated). In addition, the internal space 3A is maintained at a predetermined temperature by a heater (not illustrated).

Figure 4:
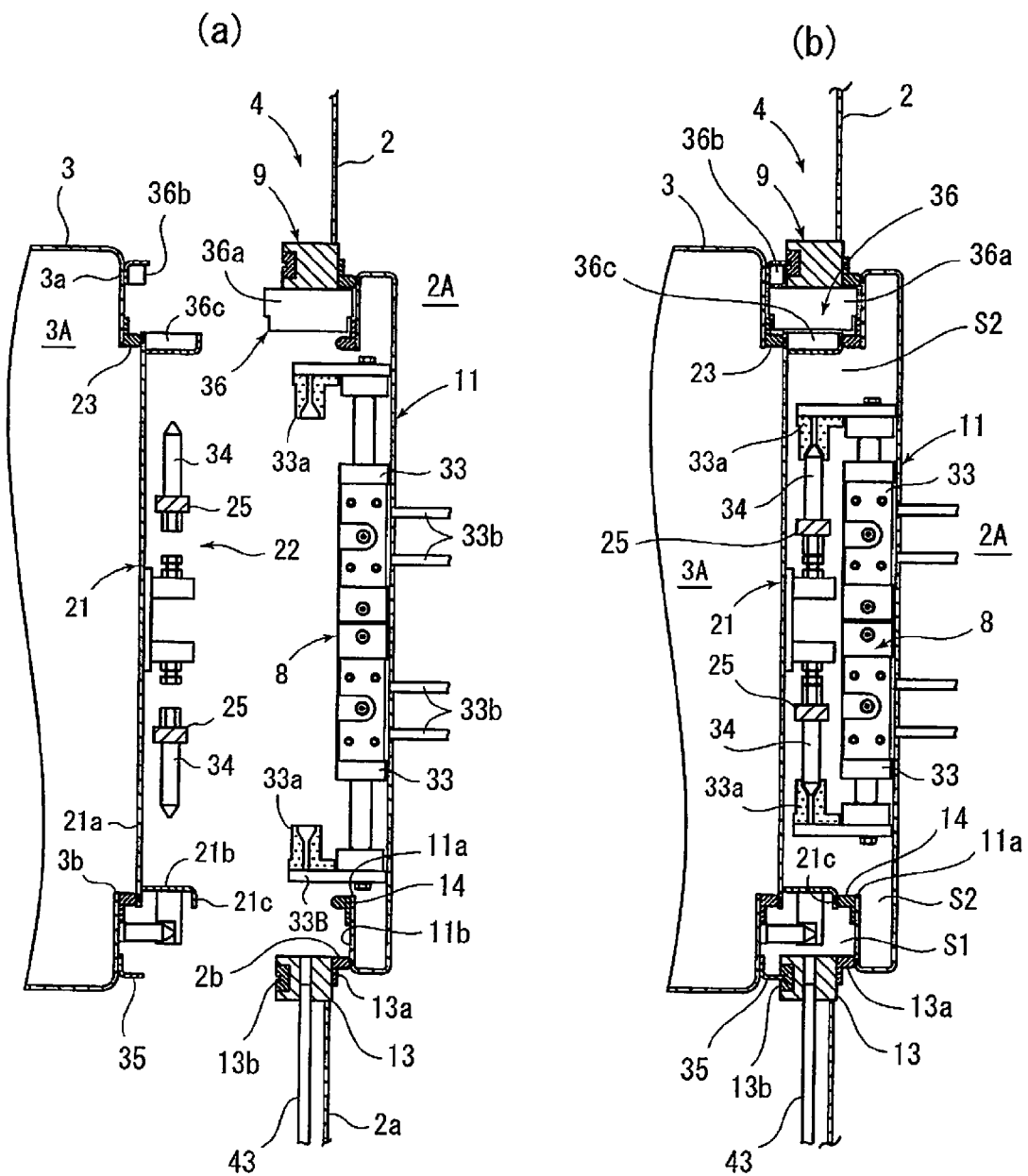
FIG. 4 (a) is a cross-sectional view illustrating a state in which the isolator and the incubator are separated, and FIG. 4 (b) is a cross-sectional view illustrating a state in which the isolator and the incubator are connected.

The isolator 2 and the incubator 3 are provided with a first opening 2b and a second opening 3b, respectively, which cause the internal spaces of the isolator 2 and the incubator 3 to communicate with each other. As illustrated in FIG. 4, the first opening 2b of the isolator 2 is closed by a first cover body 11, and the second opening 3b of the incubator 3 is closed by a second cover body 21.

The sterilized connection apparatus 4 includes a connecting unit 7 which connects the isolator 2 and the incubator 3, a cover body connecting unit 8 which couples the first cover body 11 and the second cover body 21, a sealing unit 9 which forms between the isolator 2 and the incubator 3, a decontamination space S1 isolated from an external atmosphere, and a decontamination medium supplying unit 10 which supplies a decontamination medium to the decontamination space S1.

In the sterilized connection apparatus 4, the decontamination space S1 of a small capacity having a circular shape is formed in a connecting section including the first and second openings 2b and 3b of the isolator 2 and the incubator 3 and the first and second cover bodies 11 and 21 which have been exposed to the outside, and the decontamination space S1 is decontaminated. Thus, the internal spaces of the isolator 2 and the incubator 3 can be quickly communicated with each other.

The first and second cover bodies 11 and 21, the connecting unit 7, the cover body connecting unit 8, and the sealing unit 9 will be described below with reference to FIGS. 2 to 4. FIG. 4 (a) illustrates a state in which the isolator 2 and the incubator 3 are separated, and FIG. 4 (b) illustrates a state in which the isolator 2 and the incubator 3 are connected by the connecting unit 7.

The first opening 2b is formed on a side wall 2a of the isolator 2, and the internal space 2A of the isolator 2 is isolated from an external atmosphere by the first cover body 11 which is arranged in the first opening 2b in a manner capable of being opened or closed.

The first opening 2b has a substantially rectangular shape; the four corners of the rectangle have a shape of arc. A tube-shaped circular member 13 is secured to the first opening 2b in a manner protruding from the peripheral edge of the first opening 2b to the outside while air sealing is maintained.

An inner-side sealing member 13a made of a resin material is disposed in an end section of the circular member 13 on the side of the internal space 2A of the isolator 2. An external-side sealing member 13b made of a resin material is disposed in an end section of the circular member 13 on the side of an external atmosphere.

The first cover body 11 is formed so as to have a shape of a flat box where a rectangular opening 11a facing the external side of the isolator 2 is, as illustrated in FIG. 4, formed. A flat section 11b closely attached to the inner-side sealing member 13a of the circular member 13 is disposed in an outer circumference part of the opening 11a.

A first sealing member 14 made of a resin material is disposed in a more inner circumference part of the flat section 11b relative to a contact face with the inner-side sealing member 13a. The first sealing member 14 is disposed so as to surround the opening 11a, and is closely attached to the second cover body 21 of the incubator 3.

The first cover body 11 is pivotally supported by a hinge 15 disposed on the side of the internal space 2A of the isolator 2 so that the first cover body 11 is opened toward the side of the internal space 2A of the isolator 2. An opening/closing lever 16 is also provided on the side of the internal space 2A.

The opening/closing lever 16 can be operated on the side of the internal space 2A of the isolator 2 by an operator wearing the glove 5 of the isolator 2. When the opening/closing lever 16 is engaged with a clamp 17 disposed on an inner surface of the side wall 2a, the first cover body 11 is pressed against the inner-side sealing member 13a and the internal space 2A of the isolator 2 is sealed by the first cover body 11.

The second opening 3b is formed on a side wall 3a of the incubator 3. In the second opening 3b, the second cover body 21 is arranged detachably by use of an attach/detach unit 22; thus, the internal space 3A of the incubator 3 can be isolated from an external atmosphere.

The second opening 3b of the incubator 3 is formed so as to have a substantially rectangular shape; the four corners of the rectangle have a shape of arc. A second sealing member 23 is disposed along a peripheral edge of the second opening 3b in a manner protruding to the outside.

The second cover body 21 is, as illustrated in FIG. 4, formed so as to have a shape of tray, and is constituted of: a bottom section 21a closely attached to the second sealing member 23 disposed in the second opening 3b of the incubator 3; a peripheral wall 21b erected from the peripheral edge of the bottom section 21a; and a peripheral edge face 21c formed in a manner folded back from the peripheral wall 21b to the outside.

Figure 3:
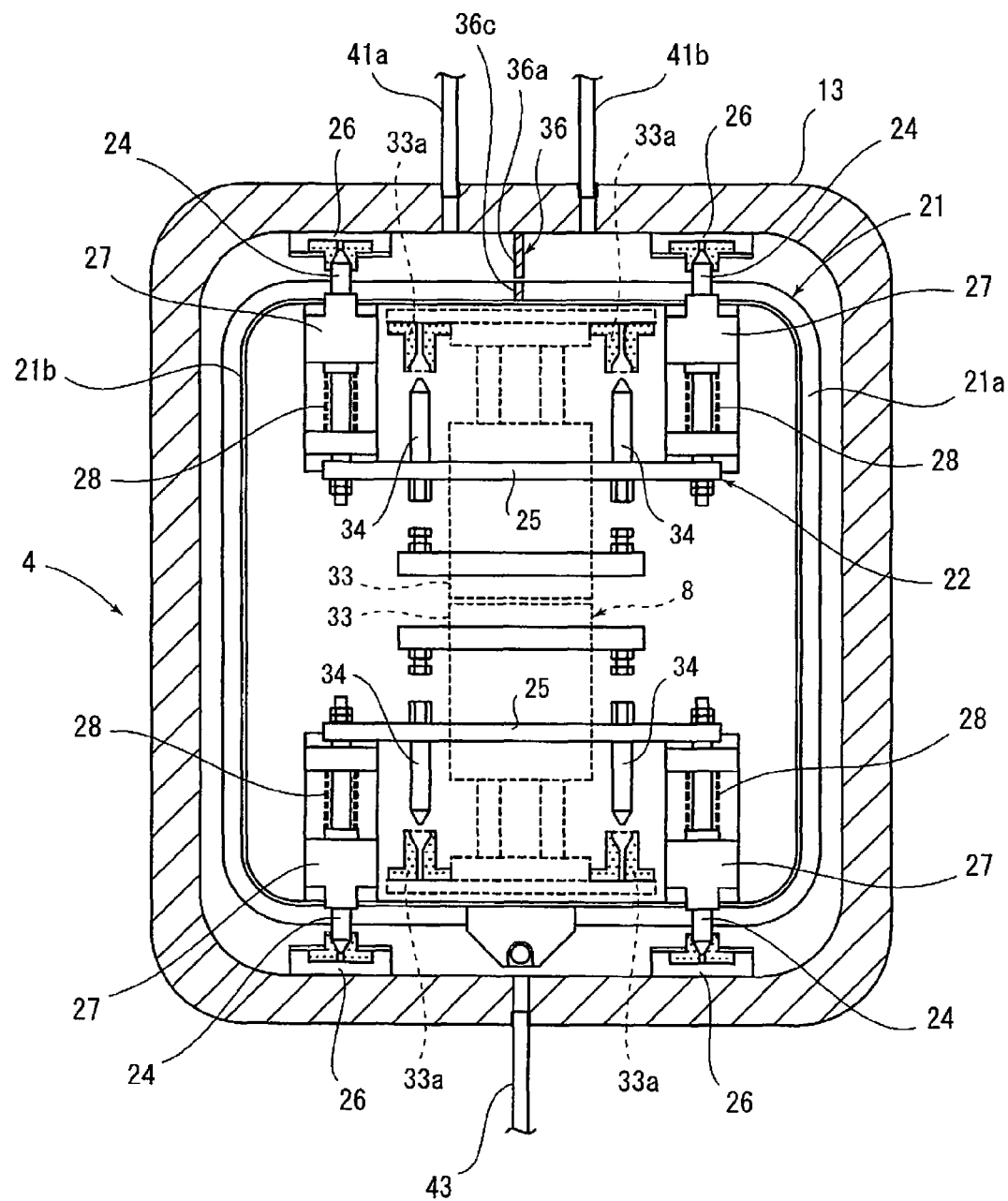
FIG. 3 is a side view illustrating the connecting state of the isolator and the incubator.

The attach/detach unit 22 includes, as illustrated in FIG. 3, four lock pins 24 (a pair of upside lock pins and a pair of downside lock pins) arranged in a manner capable of rising and setting from the peripheral wall 21b of the second cover body 21, two coupling members 25 for coupling a pair of upside lock pins 24 and a pair of downside lock pins 24, respectively, and four pin-engaging members 26 which are disposed on the side wall 3a of the incubator 3 and fit into the four lock pins 24, respectively.

The lock pins 24 are slidably arranged in a support member 27 secured to the side wall 21b of the second cover body 21 while air sealing is maintained. The lock pins 24 are biased by a spring 28 so as to protrude from the inner side to the outer side of the side wall 21b.

In this structure, when the two coupling members 25 are isolated from each other by biasing force of the spring 28, the lock pins 24 is fit into the pin-engaging members 26 and thus a state is maintained in which the bottom section 21a of the second cover body 21 is closely attached to the second sealing member 23 in the peripheral edge of the second opening 3b of the incubator 3.

On the other hand, when the two coupling members 25 are brought close to each other against the biasing force of the spring 28, the lock pins 24 withdraw from the pin-engaging members 26 and thus the second cover body 21 can withdraw from the incubator 3.

Figure 2:
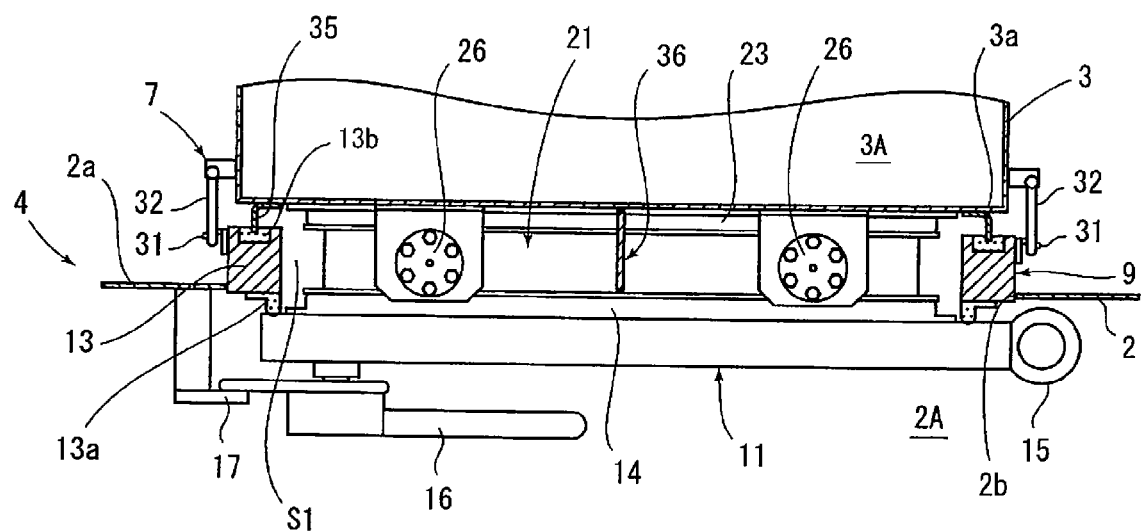
FIG. 2 is a plan view illustrating a state in which an isolator and an incubator are connected.

The connecting unit 7 includes, as illustrated in FIG. 2, a hook 31 disposed in the circular member 13 disposed in the periphery of the opening 11a of the isolator 2, and a ring 32 disposed on a side surface of the incubator 3, engaging with the hook 31. These are arranged facing each other, having the circular member 13 and the incubator 3 therebetween.

When the ring 32 is engaged with the hook 31, the isolator 2 and the incubator 3 can be coupled and fixed to each other so that the isolator 2 and the incubator 3 are not separated.

The cover body connecting unit 8 will be described below. When the isolator 2 and the incubator 3 are coupled by the connecting unit 7, the peripheral edge face 21c of the second cover body 21 is, as illustrated in FIG. 4 (b), closely attached to the first sealing member 14 disposed in the first cover body 11 of the isolator 2, and a cover body internal space S2 isolated from an external atmosphere is formed on the inner side of the first cover body 11 and the second cover body 21.

The cover body connecting unit 8 is provided with two air cylinders 33 on the inner side of the opening 11a of the first cover body 11. In the tip end of a piston rod of the air cylinder 33, four connecting sections 33a (a pair of upside connecting sections and a pair of downside connecting sections) having a conical insertion hole of a shape of concave are arranged so as to vertically move. The two insertion holes vertically face each other.

An air pipe 33b is connected to the air cylinder 33 while air sealing is maintained in the internal space 2A of the isolator 2. Air is supplied from an air supply source (not illustrated) through the air pipe 33b.

In the two coupling members 25 of the second cover body 21, two engaging pins 34 are, as illustrated in FIG. 3, erected, respectively, between the two lock pins 24. When the connecting sections 33a are vertically moved (advanced or withdrawn) by the air cylinders 33, the connecting sections 33a are fit into the engaging pins 34, respectively.

In the cover body connecting unit 8 having the above described structure, when the isolator 2 and the incubator 3 are coupled and fixed by the connecting unit 7 so that the first cover body 11 is closely attached to the second cover body 21, the connecting sections 33a are brought close to each other by the air cylinders 33.

Then, the connecting sections 33a engage with the engaging pins 34 disposed in the second cover body 21. Thereafter, when the air cylinders 33 push the engaging pins 34 so that the coupling members 25 are brought close to each other against the biasing force of the spring 28, the lock pins 24 are separated from the pin-engaging members 26 disposed in the periphery of the opening 11a of the incubator 3.

As a result, the first cover body 11 and the second cover body 21 are coupled, and the cover body internal space S2 is formed. In addition, a state is obtained in which the second cover body 21 can be separated from the incubator 3. Thus, the second cover body 21 can be opened/closed toward the internal space 2A of the isolator 2 while the first cover body 11 and the second cover body 21 are integrally coupled.

The sealing unit 9 is constituted of the circular member 13 surrounding the first opening 2b of the isolator 2 with no end section, and a protruding member 35 surrounding the second opening 3b of the incubator 3 with no end section.

In the circular member 13, the external-side sealing member 13b is disposed on a surface facing the incubator 3. The protruding member 35 is disposed so as to surround a more outer side of the pin-engaging member 26 disposed in the periphery of the second opening 3b.

In this structure, when the isolator 2 and the incubator 3 are connected by the connecting unit 7, the external-side sealing member 13b and the protruding member 35 are, as illustrated in FIG. 4 (b), closely attached to each other; formed on the inside thereof is a decontamination space S1 of a capacity of 20 to 40 L isolated from an external atmosphere.

Furthermore, the decontamination space S1 isolated by the sealing unit 9 is formed as a circular space surrounding the periphery of the first and second cover bodies 11 and 21 coupled by the cover body connecting unit 8. Thus, the decontamination space S1 and the cover body internal space S2 are prevented from communicating with each other.

The sealing unit 9 may be arranged in any of the isolator 2 and the incubator 3. For example, when a structure is used in which the protruding member 35 is used as a sealing member and directly closely-attached to a wall surface on the periphery of the first opening 2b of the isolator 2, the external-side sealing member 13b can be omitted.

According to the present embodiment, a shielding member 36 for blocking the flow of decontamination medium is arranged on the inside of the circular decontamination space S1 so that the circular decontamination space S1 is divided to form a long and thin pipe line-shaped decontamination space S1.

The shielding member 36 is, as illustrated in FIG. 3, disposed in an upper central section of the circular decontamination space S1. The shielding member 36 is, as illustrated in FIG. 4 (a), constituted of three plate-shaped members which are a member 36a secured to the circular member 13 of the isolator 2, a member 36b disposed in the protruding member 35 of the incubator 3, and a member 36c disposed on an outer circumference side of the peripheral wall 21b of the second cover body 21.

When the isolator 2 and the incubator 3 are, as illustrated in FIG. 4 (b), coupled to connect the first and second cover bodies 11 and 21, these members 36a to 36c are combined to divide the decontamination space S1.

In the shielding member 36, when the members 36a to 36c are combined, it is not required to completely close the decontamination space S1. As long as the flow of decontamination medium is blocked on the inside of the decontamination space S1, a narrow gap is permitted to be formed between the members 36a to 36c.

In the decontamination medium supplying unit 10, hydrogen peroxide vapor is supplied as a decontamination medium. This decontamination medium flows in a supply pipe line 41 disposed between the decontamination medium supplying unit 10 and the sealing unit 9 and is supplied to the decontamination space S1.

A HEPA filter 42 is arranged in the path of the supply pipe line 41. The supply pipe line 41 is branched into supply pipe lines 41a and 41b at a position adjacent to the HEPA filter 42, and is connected to an upper part of the circular member 13 constituting the sealing unit 9 at a position having the shielding member 36 therebetween.

In other words, the decontamination space S1 is divided by the shielding member 36 to form a long and thin pipe line-shaped space; and the supply pipe lines 41a and 41b are connected, respectively, to positions close to one surface and the other surface of the shielding member 36, the one surface and the other surface of the shielding member 36 constituting end sections of the decontamination space S1. Thus, a decontamination medium is supplied from both end sections of the long and thin pipe line-shaped decontamination space S1.

Connected to a lower part of the circular member 13 constituting the sealing unit 9 is a discharge pipe line 43 used to discharge gas from the inside of the decontamination space S1. In the long and thin pipe line-shaped decontamination space S1, this discharge pipe line 43 is connected between the connecting position of the supply pipe line 41a and the connecting position of the supply pipe line 41b which constitute the end sections of the decontamination space S1. The discharge pipe line 43 is provided with a HEPA filter 44 and a catalyst 45 which decomposes a decontamination medium.

A method for using the sterilized connection apparatus 4 according to the present invention will be described below. Particularly, a procedure will be described which decontaminates the decontamination space S1 after completion of connecting the isolator 2 and the incubator 3 by use of the connecting unit 7.

The isolator 2 and the incubator 3 are connected by the connecting unit 7, and the first and second cover bodies 11 and 21 are connected by the cover body connecting unit 8. Thus, the decontamination space S1 is formed by the sealing unit 9; the decontamination space S1 is formed as a circular space surrounded by the first and second cover bodies 11 and 21.

As a result, the decontamination space S1 is isolated from an external atmosphere and from the cover body internal space S2. However, the inside of the decontamination space S1 has been partially exposed to an external atmosphere. Accordingly, if nothing is done, when the first and second cover bodies 11 and 21 are opened, the internal spaces 2A and 3A of the isolator 2 and the incubator 3 may be contaminated by bacteria or the like which remain attached to the exposed part.

Thus, in the present embodiment, the decontamination space S1 is decontaminated, whereby the first and second cover bodies 11 and 21 can be opened under sterilized conditions; and after the internal spaces 2A and 3A have been made to communicate with each other under sterilized conditions, a culture material can be transferred between the isolator 2 and the incubator 3.

As described above, when the isolator 2 and the incubator 3 is connected and when the first and second cover bodies 11 and 21 are connected, the circular decontamination space S1 is formed so as to surround the periphery of the first and second cover bodies 11 and 21; further, this decontamination space S1 is formed as a long and thin pipe line-shaped space by the shielding member 36.

The supply pipe lines 41a and 41b are connected, respectively, to both ends of the long and thin pipe line-shaped decontamination space S1, that is, to positions on one side and the other side thereof sandwiching the shielding member 36. The discharge pipe line 43 is connected between the supply pipe lines 41a and 41b; according to the present embodiment, the discharge pipe line 43 is connected to an intermediate part of the pipe line shaped decontamination space S1.

In this structure, when the decontamination medium supplying unit 10 supplies a vaporized decontamination medium to the supply pipe line 41, this decontamination medium flows in from both ends of the long and thin pipe line-shaped decontamination space S1.

Thereafter, the decontamination medium flows towards the discharge pipe line 43, and is combined at the position to which the discharge pipe line 43 is connected, and is discharged from the discharge pipe line 43. As a result, the air on the inside of the decontamination space S1 is replaced with the vaporized decontamination medium. Here, since the supply pipe lines 41a and 41b are disposed close to the shielding member 36, the decontamination medium also flows towards the side of the shielding member 36, and goes back at the shielding member 36 and flows towards the side of the discharge pipe line 43.

In this way, the circular decontamination space S1 is divided by the shielding member 36 to form the long and thin pipe line-shaped space, whereby the decontamination space S1 can be quickly and uniformly filled with the decontamination medium flowing into the decontamination space S1.

In this way, after the inside of the decontamination space S1 has been filled with the decontamination medium, an electromagnetic valve is closed to stop the inflow and discharge of gas, so that the vaporized decontamination medium is held in the decontamination space S1. For example, when this state is maintained for three minutes, the vaporized decontamination medium changes to liquid droplets and adheres to members exposed to the inside of the decontamination space S1.

After holding the decontamination medium for a predetermined length of time, the decontamination medium supplying unit 10 performs aeration for supplying air containing no decontamination medium and discharging the decontamination medium from the decontamination space S1 for a predetermined length of time.

After these operations have been completed, the operator wears the glove 5 arranged in the isolator 2 and manipulates the opening/closing lever 16 from the inside of the isolator 2 to open towards the inside of the isolator 2, the first and second cover bodies 11 and 21 integrally coupled to each other, so that the internal space 2A of the isolator 2 communicates with the internal space 3A of the incubator 3.

In this state, parts exposed to the decontamination space S1 have been decontaminated and further, the cover body internal space S2 of the first and second cover bodies 11 and 21 is sealed by the cover body connecting unit 8. Accordingly, parts exposed to an external atmosphere are prevented, without being decontaminated, from being exposed to the internal spaces 2A and 3A of the isolator 2 and the incubator 3.

After the operations for the isolator 2 and the incubator 3 have been completed, the operator disconnects these connections. The operator manipulates the opening/closing lever 16 to integrally close the first and second cover bodies 11 and 21 and disconnect the connection of the first and second cover bodies 11 and 21 by the cover body connecting unit 8 so that the connection of the isolator 2 and the incubator 3 by the connecting unit 7 is disconnected.

When it is feared that cells or tissues handled in the internal space 2A of the isolator 2 may be contaminated by harmful materials such as microbes, bacteria or viruses, since the decontamination space S1 has been formed by the sealing unit 9, it is also possible to re-decontaminate the decontamination space S1 by use of the decontamination medium supplying unit 10.

Then, the operator can move this incubator 3 to a given place and connect another incubator 3 to the isolator 2.

As described above, in the sterilized connection apparatus 4 having the aforementioned structure, the isolator 2 and the incubator 3 are connected by the connecting unit 7 to form the circular decontamination space S1 surrounding the first and second cover bodies 11 and 21. Accordingly, the decontamination space S1 of a small capacity can be quickly decontaminated, so that communication of the isolator 2 and the incubator 3 is efficiently performed.

In addition, the shielding member 36 is provided on the inside of the circular decontamination space S1 to form the decontamination space S1 as a long and thin pipe line-shaped space. Also, the supply pipe lines 41a and 41b are connected to a position close to the shielding member 36 to supply a decontamination medium from one end section and the other end section of the long and thin pipe line-shaped decontamination space S1.

As a result, the decontamination medium flows, without turbulently diffusing, in one direction along the inside of the decontamination space S1 towards the discharge pipe line 43. Thus, the decontamination medium can be quickly and uniformly circulated through the whole space of the inside of the decontamination space S1.

On the other hand, when the decontamination medium is discharged from the discharge pipe line 43, the decontamination medium converges in the vicinity of the discharge pipe line 43, thus causing a turbulent flow. Accordingly, the decontamination medium can also be circulated to the outer circumference surface of the first and second cover bodies 11 and 21 facing the position at which the discharge pipe line 43 is connected.

However, when a structure is used in which the shielding member 36 is not provided (in this case, the decontamination medium is made to flow into the circular decontamination space S1 from a single supply pipe line 41), after flowing into the circular decontamination space S1, the inflowing decontamination medium does not always branch symmetrically and thus the decontamination medium may not circulate uniformly; there is a risk that a variation in decontamination effects occurs.

When a structure is used in which, while the shielding member 36 is provided to form the long and thin pipe line-shaped decontamination space S1, the supply pipe line 41 is connected to one end section of the pipe line-shaped decontamination space S1 and the discharge pipe line 43 is connected to the other end section thereof, then the decontamination medium flows in one direction but is immediately discharged from the discharge pipe line 43 at a position to which the discharge pipe line 43 is connected, posing a problem that the decontamination medium does not satisfactorily circulate to corners of the shielding member 36 lying in the part to which the discharge pipe line 43 is connected.

Figure 5:
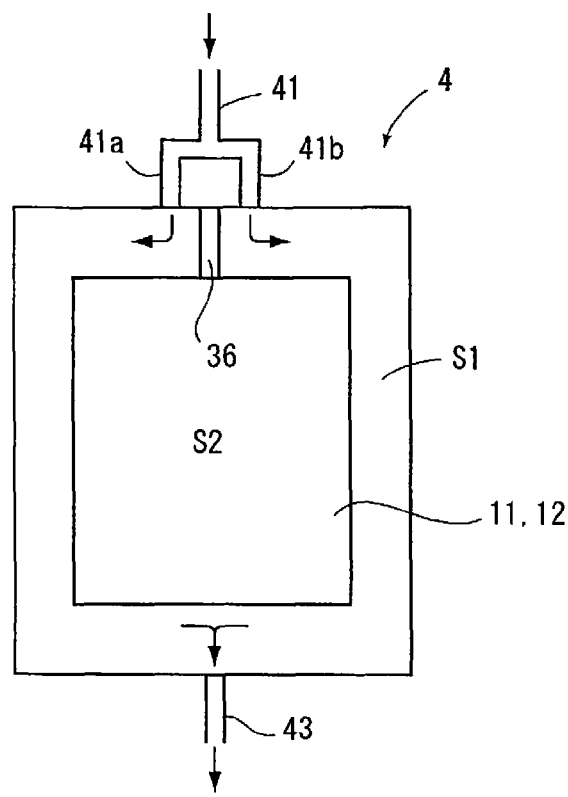
FIG. 5 is a view for explaining the configuration of the decontamination space.
Figure 6:
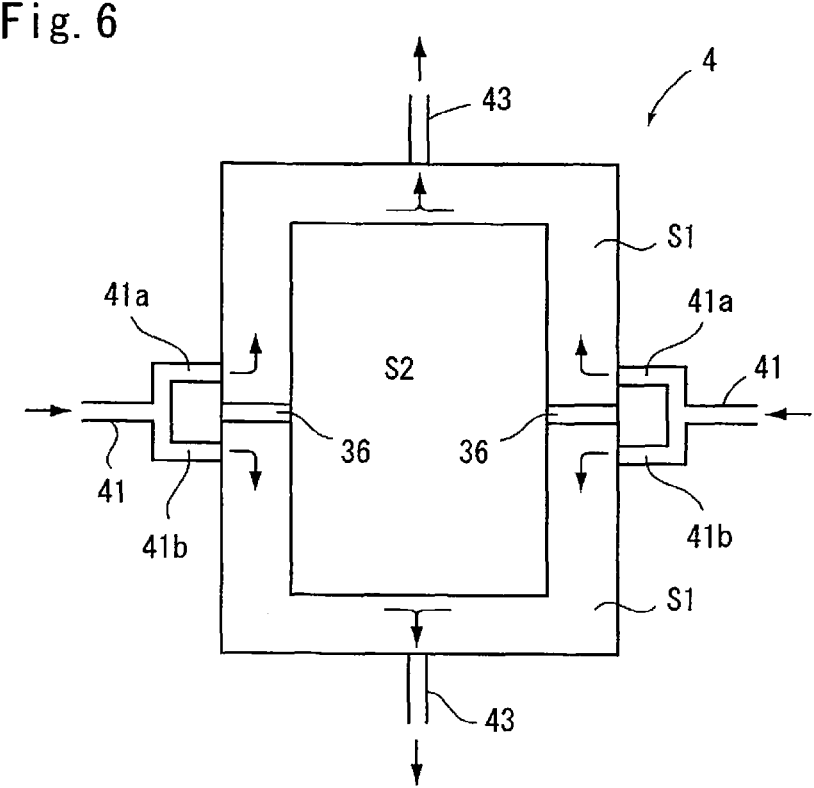
FIG. 6 is a view for explaining a decontamination space having a configuration different from that of the above described embodiment.

In FIG. 5, the structure is illustrated in which a single shielding member 36 is provided for a decontamination space. However, two or more shielding members 36 may be, as illustrated in FIG. 6, provided to form two or more long and thin pipe line-shaped decontamination spaces S1.

When two shielding members 36 are provided at an opposite position having the first and second cover bodies 11 and 21 therebetween, two long and thin pipe line-shaped spaces substantially having a shape ⊃ (an upside space and a downside space) are formed by the shielding member 36.

In this case, different shielding members 36 are disposed, respectively, in end sections of the pipe line-shaped decontamination space S1; supply pipe lines 41 are connected, respectively, to the vicinity of the shielding members 36; and discharge pipe lines 43 are connected between the connecting positions of the supply pipe lines 41 connected, respectively, to one end section and the other end section.

What is claimed is:

1. A sterilized connection apparatus comprising:

sealing means for forming between a first sealed box having an opening sealed by a first cover body and a second sealed box having an opening sealed by a second cover body, a decontamination space used to isolate the first cover body and the second cover body from an external atmosphere;

decontamination medium supplying means for supplying a vaporized decontamination medium to the decontamination space through a supply line; and a discharge pipe line for discharging the decontamination medium from the decontamination space, wherein cover body connecting means is provided for coupling the first cover body and the second cover body and forms the decontamination space as a circular decontamination space surrounding the periphery of the cover bodies, a shielding member for blocking circulation of the decontamination medium is provided on the inside of the circular decontamination space so that the circular decontamination space is divided to form a long and thin pipe line-shaped decontamination space having an end section constituted of the shielding member, and supply pipe lines are connected, respectively, to end sections of the long and thin decontamination space which sandwich the shielding member and the discharge pipe line is provided between connecting positions of the supply pipe lines.

2. The sterilized connection apparatus according to claim 1, wherein two or more shielding members are provided, and the decontamination space is divided in two or more spaces.

* * * * *